United States Patent [19]

Stirling

[11] 4,354,974
[45] Oct. 19, 1982

[54] CLAVUDIENES

[75] Inventor: Irene Stirling, Worcester Park, England

[73] Assignee: Beecham Group Limited, England

[21] Appl. No.: 747,640

[22] Filed: Dec. 6, 1976

[30] Foreign Application Priority Data

Dec. 16, 1975 [GB] United Kingdom ............... 51516/75

[51] Int. Cl.³ .................... C07D 498/04; A61K 31/42
[52] U.S. Cl. ................................. 260/245.3; 424/272
[58] Field of Search ....................... 260/307 FA, 307 F

[56] References Cited
FOREIGN PATENT DOCUMENTS
2616087 10/1976 Fed. Rep. of Germany .

OTHER PUBLICATIONS
Hackh–"Chemical Dictionary"–4th Edition (1969), McGraw-Hill Book Co.-p. 16.
Cole et al., C.A. 84,72635t (1976).

*Primary Examiner*—Mark L. Berch
*Attorney, Agent, or Firm*—Jacobs & Jacobs

[57] ABSTRACT

Esters of the compound of the formula:

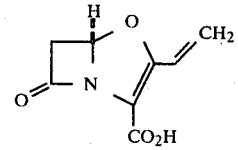

are useful for their antibacterial and β-lactamase inhibitory activity.

17 Claims, No Drawings

CLAVUDIENES

The present invention relates to novel β-lactam containing compounds, to processes for their preparation and to compositions containing them.

Belgian Pat. No. 827926 discloses inter alia that clavulanic acid, which is the compound of the formula (I):

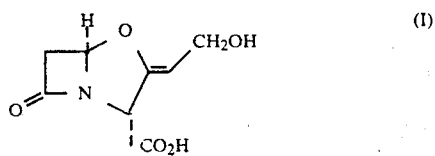

and its salts and esters possess anti-bacterial and β-lactamase inhibitory activity. It has now been found that a distinct group of β-lactam containing compounds possess anti-bacterial and β-lactamase inhibitory activity the spectrum of which differs from that of clavulanic acid.

Accordingly the present invention provides the esters of the compound of the formula (II):

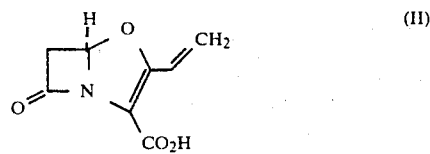

Suitable esters of the compound of the formula (II) include those corresponding to the esters of the compound of formula (I) disclosed in the aforementioned Belgian Patent. When used for the requirements of the present invention, the term "ester" comprises esters which are derived from an alcohol or a thiol of the formula ROH or RSH where R is an organic radical. As suitable R groups mention may be made of the alkyl, alkenyl, alkynyl, aryl, aralkyl or other similar groups, which may be substituted if desired. In order not to increase the molecular weight excessively, the R groups ordinarily do not contain more than 16 carbon atoms, and more particularly not more than 12 carbon atoms and preferably not more than 8 carbon atoms.

Preferably the R group is derived in principle from an alcohol ROH or (less preferably) from a thiol RSH which is pharmaceutically acceptable.

By way of suitable substituents which may be included in the R group mention may be made of halogen atoms and lower alkoxy, hydroxy, lower acyloxy, (lower)alkyl-amino, (lower)dialkylamino and similar groups. The term "lower" means that the group contains up to 6 carbon atoms and preferably up to 4 carbon atoms. Thus, for example, R can be one of the following groups: methyl, ethyl, n-propyl or isopropyl; butyl, pentyl, heptyl, octyl, nonyl, decyl, undecyl, dodecyl, all with straight or branched chain; vinyl, allyl, butenyl, cyclopropyl, cyclobutyl, cyclopentyl, cyclohexyl, cycloheptyl, cycloxenyl, cyclohexadienyl, methylcyclopentyl, methylcyclohexyl, benzyl, benzhydryl, phenylethyl, naphthylmethyl, phenyl, naphthyl, propynyl, tolyl, 2-chloroethyl, 2,2,2-trichloroethyl, 2,2,2-trifluoroethyl, acetylmethyl, benzoylmethyl, 2-methoxyethyl, 2-dimethylaminoethyl, 2-diethylaminoethyl, 2-piperidinoethyl, 2-morpholinoethyl, 3-dimethylaminopropyl, p-chlorobenzyl, p-methoxybenzyl, p-nitrobenzyl, p-bromobenzyl, m-chlorobenzyl, 6-methoxynaphthyl-2-methyl, p-chlorophenyl, p-methoxyphenyl or any similar group as well as groups which are known in the art referred to penicillin or cephalosporin to produce known esters which are easily hydrolyzed in vivo to the parent antibiotic.

Particularly suitable esters of the compound of the formula (II) include those of the formula (III):

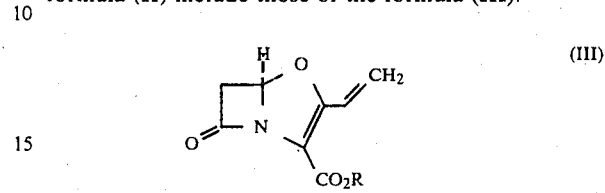

wherein R is a hydrocarbon group of up to 20 carbon atoms or an inert substituted hydrocarbon group of up to 20 carbon atoms.

Most suitably R is a group of the formula $CHR^1R^2$ wherein $R^1$ is a hydrogen atom or a hydrocarbon group of 1-6 carbon atoms and $R^2$ is a hydrogen atom or a hydrocarbon group of 1-6 carbon atoms optionally substituted by a halogen atom or a alkoxyl or acyloxyl group of up to 7 carbon atoms.

Most suitably $R^1$ is a hydrogen atom.

Most suitably $R^2$ is a phenyl group or p-methoxy phenyl group.

Preferably $CHR^1R^2$ is a benzyl group or a p-methoxybenzyl group.

Other particularly suitable esters are in-vivo readily hydrolysable esters such as the pivaloyloxymethyl, acetoxymethyl, phthalidyl, a-ethoxycarbonyloxyethyl or other such esters, for example those described in general terms in Belgian Pat. No. 827926.

The readily hydrolyzable esters include, without being limited to this, those wherein R is:

$$-\underset{\underset{A_2}{|}}{\overset{\overset{A_1}{|}}{C}}-X-CO-A_3 \quad \text{or} \quad -\underset{\underset{X--C=Y}{|}}{\overset{\overset{}{|}}{CH}}-Z$$

in which $A_1$ represents a hydrogen atom, an alkyl, aryl, or aralkyl group; $A_2$ represents a hydrogen atom or a methyl group; $A_3$ represents an alkyl, aryl, or aralkyl group; X represents oxygen or sulfur; Y represents oxygen or sulfur and Z represents a bivalent organic group. The esters which are hydrolyzed rather easily in the bloodstream after administration include those in which $A_1$ represents a hydrogen atom, $A_2$ represents a hydrogen atom or a methyl group, and $A_3$ represents a methyl, ethyl, propyl, butyl, benzyl or phenyl group, and those in which X represents oxygen, Y represents oxygen and Z represents a —$CH_2CH_2$—, —CH:CH—

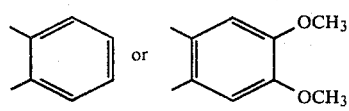

group.

The present invention also provides a pharmaceutical composition which comprises an ester of the compound of the formula (II). Such compositions also contain a conventional pharmaceutical carrier.

The compounds of formula (II) and its salts and esters are β-lactamase inhibitors which can potentiate the activity of penicillins and cephalosporins against certain β-lactamase producing organisms. Thus certain preferred compositions of this invention also comprise a penicillin or cephalosporin. In general from 50 mg to 2500 mg of a compound of this invention will be administered per day. If desired the compositions may also be used to treat infections in domestic animals such as mastitis in cows.

In a further aspect the present invention also provides a process for the preparation of the ester of the compound of the formula (II) which process comprises the removal of the elements of a compound of the formula HA from a corresponding ester of a compound of the formula (IV):

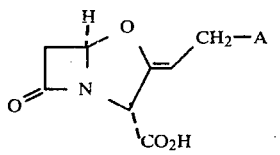
(IV)

wherein A is a hydroxyl or substituted hydroxyl group.

Suitable substituted hydroxyl groups include acylated hydroxyl groups and sulphonated hydroxyl group.

Suitable acylated hydroxyl groups A include a wide variety of acyl groups which contain up to 16 carbon atoms. Although in general, it more suitably contains up to 12 carbon atoms and is an acyl group found in the acylamino side chain of the known antibacterially active pencillins and cephalosporins. Specific acyl groups include those which are illustrated in the following list with reference to sub-formulae (a)–(d):

(a) $R_2-(C_nH_{2n})-CHX-(C_mH_{2m})-CO$ (b) $R_2-(C_nH_{2n})-Y-(C_mH_{2m})-CO$ (c) $R_3-(C_mH_{2m})-CO$ (d) 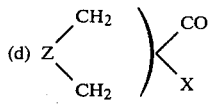

wherein X is amino, ureido, hydroxy, carboxy, esterified carboxy, azido, triazolyl, tetrazolyl, chlorine or the like; Y is oxygen or sulphur; Z is oxygen or sulphur or $(CH_2)_g$ where g is 0, 1, 2 or 3; n is 0–8; m is 0–2; $R_2$ is hydrogen cycloalkyl of 3–6 carbon atoms, alkenyl of 2–4 carbon atoms, alkynyl of 2–4 carbon atoms, cycloalkyl of 3–6 carbon atoms, phenyl, naphthyl, pynidyl, thienyl, tetrazolyl, sydnonyl, hydroxyphenyl, 3-chloro-4-hydroxyphenyl, cyano or the like, and $R_3$ is hydrogen, alkyl of 1–10 carbon atoms, alkenyl of 2–10 carbon atoms, alkynyl of 2–10 carbon atoms, phenyl, 2,6-dimethoxyphenyl, 4-hydroxyphenyl, pyridyl, thienyl, sydnonyl, naphthyl, 2-isoproxynaphthyl, 3-(2-chloro-6-fluoro)phenyl-5-methylizoxazol-4-yl and the like.

Particular acyl groups which may be considered worthy of mention include those of the formula $CO.R_4$ where $R_4$ is a methyl, ethyl, propyl, hexyl, benzyl, phenyl, cyanomethyl, phenoxcymethyl, α-phenoxyethyl, 4-pyridylmethyl, 4-pyridylthiomethyl, 2-thienylmethyl, 3-thienylmethyl, α-hydroxybenzyl, α-aminobenzyl, α-amino-p-hydroxybenzyl, α-ureidobenzyl, sydnonylmethyl, tetrazolylmethyl, α-carboxybenzyl, α-methoxycarbonylbenzyl, α-phenoxcarbonylbenzyl, 2-indanyloxybenzyl and the like groups.

Suitable sulphonated hydroxyl groups include those of the formula $OSO_2R'$ wherein $R'$ is an optionally substituted alkyl group of 1 to 4 carbon atoms, phenyl or tolyl, or a group O—H+M wherein M is a tertiary amine. Suitable substituents for $R'$ are chlorine, bromine or fluorine atoms or methoxy, ethoxy or acetoxy groups. Preferred values for $R'$ include methyl, ethyl, phenyl, tolyl, chlorophenyl and methoxyphenyl. Other preferred values for R include O—H+M groups wherein M is a pharmaceutically acceptable tertiary amine group that can complex with sulphur trioxide and contain up to 13 carbon atoms. Suitable such tertiary amine groups include trimethylamine, dimethylamine, pyridine, N-methylpiperidine and N-methylmorpholine groups.

One preferred group of sulphonated hydroxyl groups include those of the formula $OSO_2R''$ wherein $R''$ is a methyl, phenyl or tolyl group.

A second preferred group are those of the formula $OSO_2O^{\ominus\oplus}HH^1$ wherein $M^1$ is a trimethylamine, dimethylalanine, pyridine, N-methylpyridine or N-methylmorpholine group. Preferably $M^1$ is a trimethylamine group.

The preceding eliminations are normally carried out under anhydrous conditions and usually in the presence of an acid or base catalyst. Such reactions are normally carried out in an aprotic inert solvent such as dimethylsulphoxide, methylene chloride, dimethylformamide, tetrahydrofuran or the like and at a non-extreme temperature, for example from 0° C. to 25° C. such as 12°–20° C.

When the preceding reaction is carried out on a compound of the formula (IV) wherein A is a hydroxyl group the reaction is normally performed in the presence of an acid catalyst and/or a dehydration promoting agent. Suitable acid catalysts include anhydrous weak mineral acids such as orthophosphoric acid. Suitable dehydrating agents include conventional mild agents such as dicyclohexylcarbodiimide and its chemical equivalents.

When the preceding reaction is carried out on an ester of a compound of the formula (IV) wherein A is an acylated hydroxyl group the reaction is normally performed in the presence of a base; for example a tertiary amine such as triethylamine or its chemical equivalent or base of low nucleophilicity such as 1,5-diazabicyclo[5,4,0]undec-5-ene or its chemical equivalent.

It can be advantageous to include a stabilizer during the preparation of the compounds of this invention. Suitable stabilizers include hydroquinone.

The compounds of this invention are also useful intermediates in the preparation of compounds similar to those of formula (I) in which the hydroxyl group is replaced by a dibenzylamino, diallylamine or similar group. The following reaction illustrates this point:

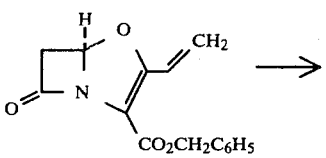

-continued

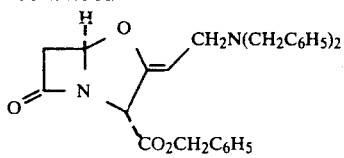

The benzyl ester of the diene (271 mg) in dry acetonitrile (4 ml) at 0° C. was treated with dibenzylamine (197 mg) in dry acetonitrile (2 ml) over 5 minutes. The reaction mixture was stirred for 2 hours at 0° C. and for a further 2 hours at room temperature (about 16° C.). The solvent was removed by evaporation and the residue dissolved in ethylacetate, washed in the water, dried, evaporated and fractioned on silica-gel to yield benzyl dibenzylaminodeoxy clavulanate which was further purified by chromatography. The resulting compound is a potent inhibitor of Staphyloccocal β-lactamase able to enhance the effectiveness of amoxycillin against organisms producing that enzyme.

EXAMPLE 1

Benzyl-7-oxo-3-vinyl-4-oxa-1-azabicyclo[3,2,0]hept-2-ene-2-carboxylate

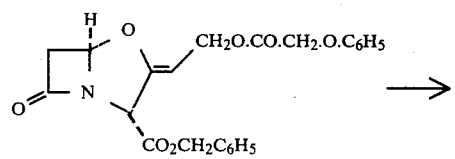

Benzylclavulanate (0.2 g) was added to dry dimethylsulphoxide (6 ml) and dry benzene (3 ml) containing dicyclohexylcarbodiimide (0.43 g). Anhydrous orthophosphoric acid (0.069 g) in dimethyl sulphoxide (2 ml) was added and the mixture stirred at room temperature for 4 hours. Thin layer chromatography showed a faster moving spot which gave a blue fluorescence at 366 n.m. The dicyclohexylurea was filtered off and benzene added to the filtrate, the organic phase was washed with water, dried and evaporated. Fractionation on silica gel gave the product as a colourless oil in 71% yield. The diene was stored as a solution in acetone containing hydroquinone (0.01%) as a stabiliser.

I.r. (film): 1810, 1700, 1628, 1565 cm$^{-1}$; n.m.r. [(CD$_3$)$_2$CO]: 3.5 (1H, dd, J 17 Hz, J' 1.5 Hz, 6β-H); 3.86 (1H, dd, J 17 Hz, J' 3 Hz, 6α-H); 5.25 (2H, s, C$\underline{H}_2$Ph); 5.62 (1H, dd, J 11 Hz, J' 2 Hz,

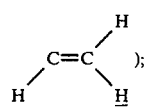

5.88 (1H, dd, J 17.5 Hz, J' 2 Hz,

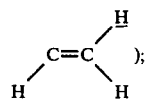

5.98 (1H, dd, J 3 Hz, J' 1.5 Hz, 5-H); 7.08 (1H, dd, J 17.5 Hz, J' 11 Hz, C$\underline{H}$=CH$_2$); 7.37 (5H, m, aromatic —H). The mass spectrum showed a molecular ion at m/e 271 (C$_{15}$H$_{13}$NO$_4$ requires 271).

EXAMPLE 2

Benzyl-7-oxo-3-vinyl-4-oxa-1-azabicyclo[3,2,0]hept-2-ene-2-carboxylate

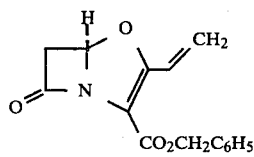

The title compound was formed quantitatively by the action of base on acyl derivatives of clavulanate. Benzyl phenoxyacetyl clavulanate was dissolved in methylene chloride and one equivalent amount of 1,5-diazabicyclo[5,4,0]undec-5-ene added; the reaction, which was complete in 10 minutes, was monitored by thin layer chromatography and i.r. and indicated that the product was identical with that obtained in Example 1.

EXAMPLE 3

Benzyl Clavudiene

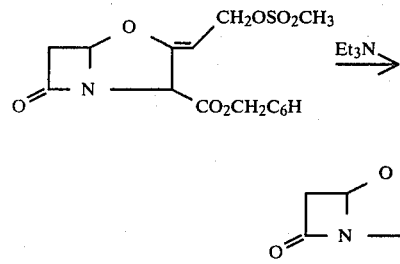
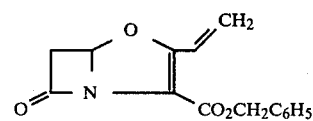

Triethylamine (1.5 g) was added to a solution of benzyl clavulanate (2.89 g) in methylene chloride (60 ml) at −10°. Methane sulphonyl chloride (1.26 g) was added slowly over 5 mins. The reaction mixture was stirred at −10° for 15 mins and washed with 5 M hydrochloric acid (ice-cold), saturated sodium bicarbonate (ice-cold), dried and evaporated. Column chromatography gave a 25% yield of benzyl clavudiene (i.r., n.m.r, t.l.c. as Example 1).

EXAMPLE 4

Methyl Clavudiene

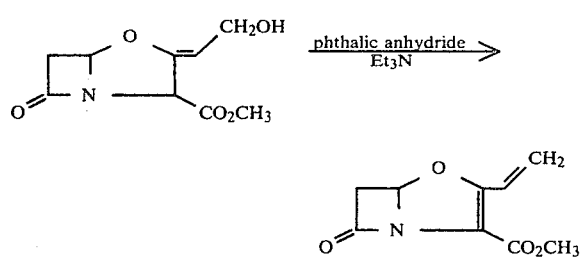

Methyl clavulanate (213 mg; 0.001 mol) in acetonitrile (10 ml) was treated with phthalic anhydride (148 mg; 0.001 mol) and triethylamine (400 mg; 0.004 mol) at 0°. After 10 mins ethyl acetate was added and the solution concentrated, a small amount of hydroquinone was added at this stage as stabilizer, more ethylacetate was added and the solution stirred with silica gel (5 g). The mixture was filtered and more silica gel (5 g) added to the filtrate also a small amount of hydroquinone, the suspension was stirred and the silica gel was filtered off. Evaporation of the solvent gave methyl clavudiene as a pale yellow oil in 50% yield.

Mass spectrum showed a molecular ion at m/c 195.i.r. ($CHCl_3$) 1805, 1710, 1635, 1575 $cm^{-1}$.

n.m.r. ($CDCl_3$) 3.42 (1H, dd, J 17H3, J 1.5H3, 6β-H) 3.73 (1H, dd, J 17H3, J 3H, 6α—CH) 3.8 (3H, S, $CO_2CH_3$), for

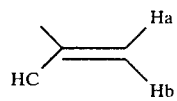

5.58 (1H, dd, J 11 Hz, J 2 Hz, Hb) 5.87; (1H, dd, J 17 Hz, J 2 Hz, Ha) 5.88; (1H, m, 5-H) 7.01 (1H, dd, J 17H, J 11 Hz, Hc).

EXAMPLE 5

Phthalidyl Clavudiene

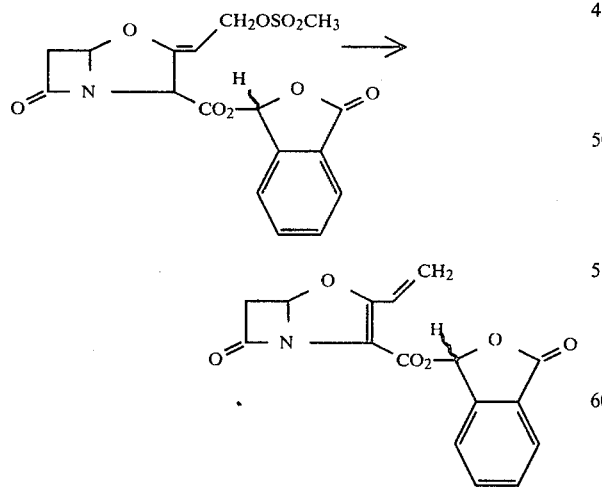

Phthalidyl clavulanate (331 mg; 0.001 mol) was dissolved in $CH_2Cl_2$ and cooled to −15°. Triethylamine (150 mg; 0.0015 mol) was added followed by methane sulphonyl chloride (126 mg; 0.0015 mol). The solution was stirred at this temperature for 2 hours, washed with 5 M hydrochloric acid (ice-cold), saturated sodium bicarbonate (ice-cold) and water (ice-cold), dried and evaporated to give the product as a pale yellow solid in 45% yield.

i.r. (Nujol) 1795, 1770, 1708 $cm^{-1}$.

n.m.r. ($CDCl_3$) 3.43 (1H, two d, J 17.5 Hz, 6β-H, two epimers) 3.72 (1H, two dd, J 17.5 Hz, 6α—H, from both epimers) 5.8 (2H,m, CH=$CH_2$, both epimers) 5.87 (1H, m, 5—H, both epimers) 7.0 (1H, m, CH=$CH_2$, both epimers) 7.41 (1H, s, $CO_2CH$) 7.63 (4H, m, aromatic-H).

EXAMPLE 6

Phthalidyl Clavudiene

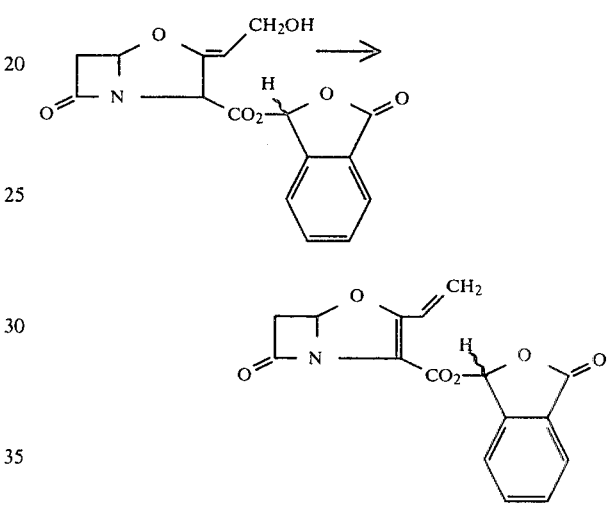

Phthalidyl clavulanate (460 mg; 0.0014 mol) in acetonitrile (10 ml) was treated with phthalic anhydride (206 mg; 0.0014 mol) at 0°. Triethylamine (566 mg; 0.0056 mol) was added dropwise over 5 mins. After 15 mins the reaction was complete (t.l.c.). The reaction mixture was worked up as described previously and the required product was obtained in 35% yield.

EXAMPLE 7

Pivaloyloxymethyl clavudiene

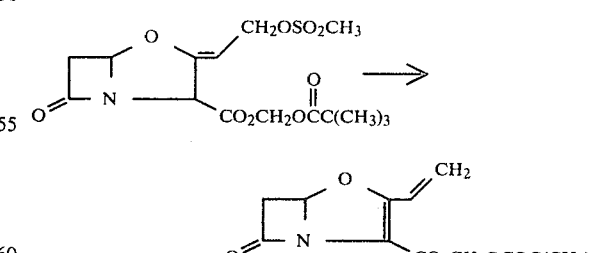

Triethylamine (150 mg) and methane sulphonyl chloride (126 mg) were added to a cold (−10°) solution of pivaloyloxymethyl clavulanate (313 mg) in methylene chloride. The reaction mixture was stirred for 30 mins and worked up as described previously to give the product as an oil in 56% yield.

EXAMPLE 8

Pivaloyloxymethyl clavudiene

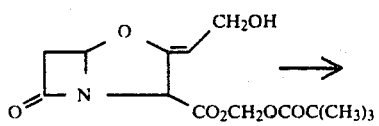

Pivaloyloxymethyl clavulanate (313 mg) in acetonitrile (10 ml) was treated with phthalic anhydride (148 mg) and triethylamine (400 mg) at 0°. Ethyl acetate (20 ml) was added and the solution treated with silica gel as previously described; also 0.01% hydroquinone was added as stabilizer. Evaporation of the solvent gave the diene as a colourless oil in 56% yield.

i.r. (film) 1810, 1750, 1720 cm$^{-1}$.

n.m.r. (CDCl$_3$) 1.22 (9H, s, C(C$\underline{H}$$_3$)$_3$ 3.45 (1H, dd, $\underline{J}$ 17 Hz, J 2 Hz, 6β-H) 3.79 (1H, dd, J 17 Hz, J 2.5 Hz, 6α-$\underline{H}$) 5.84 (2H, m CO$_2$C$\underline{H}$$_2$CO$_2$) 5.88 (1H, m, 5-$\underline{H}$, obscured by m at 5.84) for:

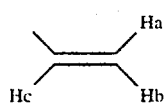

5.63 (1H, dd, $\underline{J}$ 11 Hz, $\underline{J}$ 2 Hz, Hb); 5.92 (1H, dd, $\underline{J}$ 17 Hz, $\underline{J}$ 2 Hz, Ha); 6.97 (1H, dd, $\underline{J}$ 17 Hz, $\underline{J}$ 11 Hz, Hc).

EXAMPLE 9

Methyl clavudiene

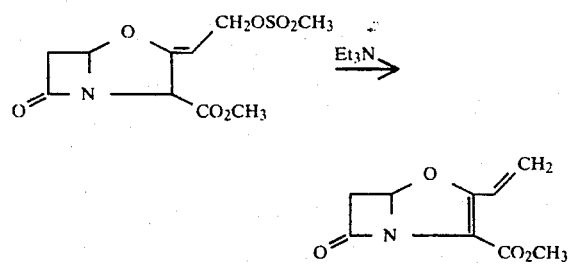

A cold (−10°) solution of methyl clavulanate in methylene chloride was treated with triethylamine (150 mg; 0.0015 mol) and methanesuphonyl chloride (126 mg; 0.0015 mol). The reaction mixture was stirred at this temperature for 45 mins and washed with ice-cold 5 M hydrochloric acid, saturated sodium bicarbonate and water then dried over magnesium sulphate and filtered. Hydroquinone was added to the filtrate which was evaporated to yield the product in 55% yield (i.r. n.m.r. as in Example 4).

What we claim is:

1. A compound of the formula:

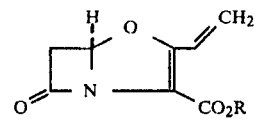

wherein R is unsubstituted alkyl, alkenyl or alkynyl of not more than 16 carbon atoms.

2. A compound according to claim 1 wherein R is methyl, ethyl, n-propyl, isopropyl, butyl, pentyl, heptyl, octyl, nonyl, decyl, undecyl, dodecyl, vinyl, allyl, butenyl or propynyl.

3. The compound according to claim 2 wherein R is methyl.

4. A compound of the formula:

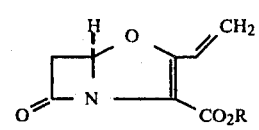

wherein R is alkyl containing a total of not more than 16 carbon atoms substituted by up to 3 halo atoms, or mono-substituted by alkoxy of up to 6 carbon atoms, hydroxy, alkylamino of up to 6 carbon atoms or dialkylamino of up to 6 carbon atoms in each alkyl group.

5. A compound according to claim 4 wherein R is 2-chloroethyl, 2,2,2-trichloroethyl, 2,2,2-trifluoroethyl, 2-methoxyethyl, 2-dimethylaminoethyl, 2-diethylaminoethyl, or 3-dimethylaminopropyl.

6. A compound of the formula:

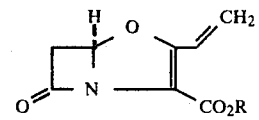

wherein R is cyclopropyl, cyclobutyl, cyclopentyl, cyclohexyl, cycloheptyl, cyclohexenyl, cyclohexadienyl, methylcycloopentyl or methycyclohexyl.

7. A compound of the formula:

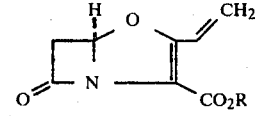

wherein R is phenyl, naphthyl, tolyl, p-chlorophenyl or p-methoxyphenyl.

8. A compound of the formula:

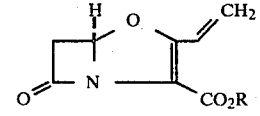

wherein R is benzhydryl, phenylethyl, naphthylmethyl, 6-methoxynaphth-2-ylmethyl, benzyl, p-nitrobenzyl, p-chlorobenzyl, p-methoxybenzyl, p-bromobenzyl or m-chlorobenzyl.

9. A compound according to claim 8 wherein R is benzyl, p-nitrobenzyl, p-chlorophenyl, p-methoxybenzyl, p-bromobenzyl or m-chlorobenzyl.

10. The compound according to claim 9 wherein R is benzyl.

11. A compound of the formula:

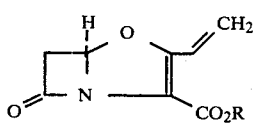

wherein R is

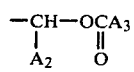

in which $A_2$ is hydrogen or methyl and $A_3$ is alkyl of 1 to 4 carbon atoms, phenyl or benzyl.

12. A compound according to claim 11 wherein R is pivaloyloxymethyl or acetoxymethyl.

13. A compound of the formula:

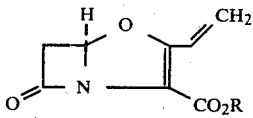

wherein R is

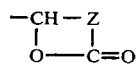

wherein Z is ethylene, vinylene, 1,2-phenylene or 4,5-dimethoxy-1,2-phenylene.

14. The compound according to claim 13 wherein R is phthalidyl.

15. A compound of the formula:

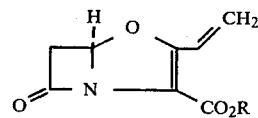

wherein R is acetylmethyl, benzoylmethyl or α-ethoxycarbonyloxyethyl.

16. The compound according to claim 15 wherein R is α-ethoxycarbonyloxyethyl.

17. The compound of the formula:

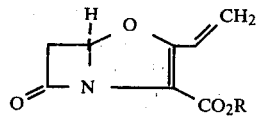

wherein R is methyl, pivaloyloxymethyl, benzyl, phthalidyl, acetoxymethyl, α-ethoxycarbonyloxyethyl, p-nitrobenzyl, p-methoxybenzyl, p-chlorobenzyl, p-bromobenzyl, or m-chlorobenzyl.

* * * * *